United States Patent [19]

Lecloux et al.

[11] 4,353,832

[45] Oct. 12, 1982

[54] PROCESS FOR THE PREPARATION OF CARBOXYL COMPOUNDS

[75] Inventors: André Lecloux, Meise; Claude Declerck, Brussels; Franz Legrand, Quaregnon, all of Belgium

[73] Assignee: INTEROX (Societe Anonyme), Brussels, Belgium

[21] Appl. No.: 157,274

[22] Filed: Jun. 5, 1980

[30] Foreign Application Priority Data

Jun. 29, 1979 [FR] France .............................. 79 17307

[51] Int. Cl.$^3$ .................... C07D 313/04; C07C 51/16; C07C 51/235; C07C 67/39
[52] U.S. Cl. ................................ 549/272; 560/238; 562/531; 562/533; 549/263; 549/273
[58] Field of Search ....................... 260/343; 560/238; 562/531, 533

[56] References Cited

U.S. PATENT DOCUMENTS

3,457,298 7/1969 Schmerling .................... 260/476

FOREIGN PATENT DOCUMENTS

2372161 6/1978 France .
753686 7/1956 United Kingdom .
1050846 12/1966 United Kingdom .

OTHER PUBLICATIONS

Hudlicky, *Coll. Czech. Chem. Commun.*, vol. 16, pp. 283-295 (1951).

*Primary Examiner*—John M. Ford
*Attorney, Agent, or Firm*—Spencer & Kaye

[57] ABSTRACT

A process for the production of carboxyl compounds such as caprolactones, in which the corresponding carbonyl compounds are oxidized with hydrogen peroxide in the presence of a catalyst in a substantially anhydrous liquid medium. The water formed by the reaction and any water introduced into the reaction mixture are removed from the reaction mixture.

13 Claims, 1 Drawing Figure

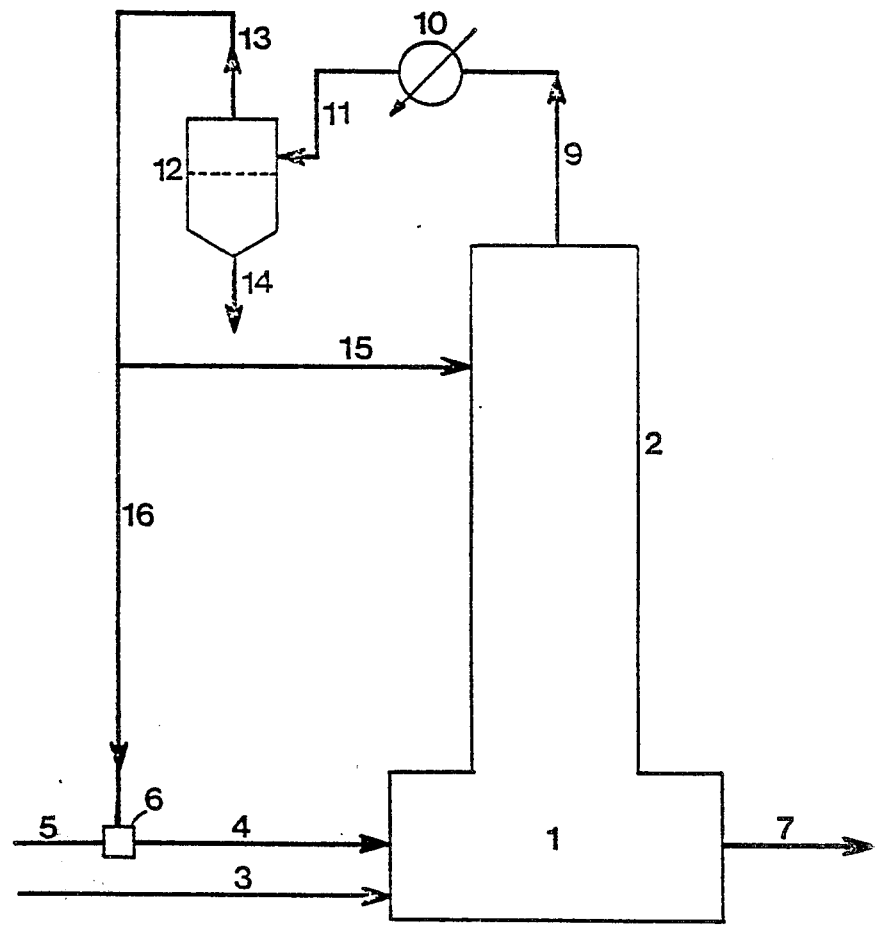

PROCESS FOR THE PREPARATION OF CARBOXYL COMPOUNDS

BACKGROUND OF THE INVENTION

The present invention relates to a process for the preparation of carboxyl compounds such as esters, lactones and carboxylic acids from the corresponding carbonyl compounds. More particularly it relates to a process for the preparation of lactones, and more especially still to a process for the preparation of caprolactone, by reaction of the corresponding ketones with hydrogen peroxide.

Lactones are in general prepared by oxidation of the corresponding cyclic ketones by means of percarboxylic acids. This technique, though very efficient, requires the preliminary preparation of the peracids, for example by direct oxidation of the corresponding aldehyde. Furthermore, the presence of the percarboxylic acids and of the corresponding carboxylic acids in the reaction mixture results in the formation of relatively large amounts of by-products derived therefrom.

In order to simplify the reaction scheme, it has been proposed, in British Pat. No. 1,050,846 filed on Sept. 16, 1964 in the name of Imperial Chemical Industries Ltd., to react a cyclic ketone, such as cyclohexanone, directly with hydrogen peroxide in the presence of a catalyst consisting of an oxyacid of an element of a long period of groups IV to VI of the periodic table of the elements. However, the amounts of catalyst employed are very high. Furthermore, the yields of caprolactone from this known process are very low, probably because of the formation of hydroxycaproic acid. This latter product, which cannot easily be converted to caprolactone, proves to be very troublesome if the caprolactone is used for the preparation of polymers such as polyesters, polyols and polyurethanes.

SUMMARY OF THE INVENTION

The object of the present invention is to provide a process for the preparation of carboxyl compounds which makes it possible to overcome the abovementioned disadvantages of the known processes and, in particular, to obtain the carboxyl compound with good selectivity and in a single stage, without the prior preparation of intermediate reactants such as percarboxylic acids.

The process according to the invention furthermore makes it possible to achieve very high reaction rates, which in turn makes it possible to increase substantially the productivity of the reactors. Furthermore, it results in long working lives of the catalysts employed. In addition, the process makes it possible easily to remove the heat of reaction, and requires lower energy consumption. Moreover, the separation of the reaction mixture, resulting from the process, into its various constituents is greatly simplified because there is no carboxylic acid by-product.

The process according to the invention can also easily be carried out continuously and very safely, because it does not require the use of highly concentrated solutions of peroxidic compounds.

To achieve these and other objects, the invention provides to a process for the preparation of carboxyl compounds by reaction of the corresponding carbonyl compound with hydrogen peroxide in a liquid medium and in the presence of a catalyst, wherein the liquid reaction mixture is kept in a substantially anhydrous state.

BRIEF DESCRIPTION OF THE DRAWINGS

The single drawing FIGURE is a schematic diagram of an apparatus for continuously carrying out the process of the invention.

DETAILED DESCRIPTION OF THE INVENTION

The liquid reaction mixture in which the carbonyl compound is reacted is considered to be substantially anhydrous if it contains less than 5% by weight of water. Preferably, a water concentration of less than 2% by weight of the mixture is maintained in the liquid reaction mixture. Very good results have been obtained if the reaction mixture contains less than 1% by weight of water.

In order to keep the mixture in a substantially anhydrous state, the water entering the mixture is removed continuously. This water in general consists of the water formed by the reaction, and the water which may be introduced with the reactants. Various techniques may be used for this continuous removal. In general, the water present in the reaction mixture is removed by vaporization processes such as distillation, azeotropic distillation or entrainment by means of an inert gas.

If the water forms a minimum boiling point azeotrope with one of the constituents of the mixture, such as the carbonyl compound or the possible solvent, namely an azeotrope of which the boiling point is lower than that of the other constituents of the mixture and of the other azeotropes which may possible form, the water is in general removed by azeotropic distillation. This technique is very particularly suitable if the azeotrope thus formed is a heterogeneous azeotrope, because it is then possible to recycle the organic phase to the reaction mixture after having removed the aqueous phase of the distillate.

If the boiling point of water is lower than that of the other constituents of the reaction mixture and of the azeotropes which may possibly form, a process of distillation, or a process of entraining the water by continuously passing an inert gas through the reaction mixture, is most commonly used. The latter technique is in general used if it is desired to avoid raising to the boil mixtures which are prone to decompose at their boiling point.

The carbonyl compounds which can be used in the process according to the invention can be of very diverse types. In general, they are selected from among the substituted or unsubstituted, saturated or unsaturated ketones and aldehydes of the aliphatic or alicyclic type, and can contain one or more carbonyl groups.

The process according to the invention is in general applied to carbonyl compounds containing from 4 to 30 carbon atoms and preferably from 5 to 26 carbon atoms. The process can thus advantageously be applied to substituted or unsubstituted cyclopentanones and cyclohexanones, such as cyclopentanone, benzylidenecyclopentanone, cyclohexanone, bromocyclohexanone, chlorocyclohexanone, methylcyclohexanone and benzylidenecyclohexanone, to other cyclic ketones such as cyclohexenone, cyclooctanone, isophorone, fluorenone, cyclododecanone, bicyclooctanone, methylbenzoquinone, norcamphor, the naphthoquinones, muscone and camphor, to methyl ketones such as methyl cyclobutyl ketone, methyl cycloheptyl ketone, methyl n-hexyl ketone, methyl cyclopropyl ketone, methyl isobutyl ketone, acetophenone, acetylmethylcyclopentane, acetylmethylcyclohexane and pinacolone, to other linear ketones such as nitrobenzophenone, benzophenone, methoxybenzophenone and cyclohexyl phenyl ketone, ketosteroids (compounds possessing a substituted cyclopentanophenanthrene skeleton) and keto-alcohols, as well as to aldehydes such as vanillin, heptanal, benzaldehyde and the aldoses.

The process according to the invention is very suitable for the oxidation of ketones. It is particularly suitable for the oxidation of cyclic ketones, that is to say ketones in which the carbonyl group forms part of the ring.

Good results have been obtained when applying the process according to the invention to cyclohexenones, cyclopentanones, methylcyclohexanones, heptanal and, very especially, cyclohexanone.

The oxidation of aldehydes by the process according to the invention leads to the formation of the corresponding carboxylic acids. The oxidation of the ketones leads to the formation of esters. In the latter case, if the ketone employed is a cyclic ketone, the product obtained is an internal ester, generally referred to as a lactone.

The hydrogen peroxide can be employed in the process according to the invention in the form of aqueous solutions or solutions in an organic solvent. For economic reasons, aqueous solutions of hydrogen peroxide are generally employed. These can have very varying concentrations of hydrogen peroxide. In general, the aqueous solutions of hydrogen peroxide contain more than 10% by weight of hydrogen peroxide. Lower concentrations are less frequently used because they necessitate the removal of large amounts of water. In general, the solutions do not contain more than 90% of hydrogen peroxide. Solutions of higher concentration can be used but they are difficult to produce and rather dangerous to use. Preferably, solutions containing from 20 to 85% by weight of hydrogen peroxide are used.

In the reaction mixture employed according to the invention, the proportions of the reactions can vary within very wide limits, depending on the chosen speeds of introduction of the reactants, the rate of reaction, the possible use of an inert solvent and the possible removal of water by distillation of an azeotrope of water and the carbonyl compound. Thus, the number of mols of hydrogen peroxide in the reaction mixture in general does not exceed twice the number of mols of carbonyl groups. Good results have been obtained if a deficiency of hydrogen peroxide relative to the carbonyl compound is maintained in the reaction mixture, so as to achieve a molar ratio of hydrogen peroxide to carbonyl compound not exceeding 0.9.

In general, a low concentration of hydrogen peroxide, which may be as little as 0.0001% by weight or even less, is maintained in the reaction mixture. At the start of the reaction, the proportion of hydrogen peroxide present in the reaction mixture employed is in general between 0.001 and 10% of its weight and the proportion of carbonyl compound is in general between 5 and 99.9% by weight. If the reaction mixture employed does not contain an inert solvent, the proportion of the carbonyl compound is most commonly between 90 and 99.9% by weight.

The molar ratio of hydrogen peroxide relative to the fresh carbonyl compound (excluding the recycled product) fed to the reactor is in general close to the stoichiometric ratio and is most frequently between 0.5 and 1.5.

The catalysts used in the process according to the invention are in general selected from among the Friedel-Crafts catalysts and their mixtures. Among these, the Lewis acids are most commonly used in preference to the Brönsted acids. In general, the catalysts used are compounds of metals selected from amongst beryllium, magnesium, the elements of groups IIb, IIIa and b, IVb, Vb, VIb and VIII and the elements of periods 3, 4, 5 and 6 of groups IVa, Va and VIa, or compounds of hydrogen fluoride. Good results have been obtained with compounds of metals selected from among beryllium, zinc, cadmium, boron, aluminum, gallium, indium, scandium, yttrium, lanthanum, silicon, germanium, tin, titanium, zirconium, hafnium, thorium, antimony, bismuth, vanadium, niobium, tantalum, tellurium, chromium, molybdenum, tungsten, iron and ruthenium. The compounds of titanium, tantalum, tungsten, tin, molybdenum, antimony, boron and zinc have given excellent results.

The metal compounds used as catalysts may be of various types. They are in general selected from among the fluorides, chlorides, oxychlorides, oxyfluorides, perchlorates and fluoroalkanesulphonates, as well as their complexes.

The preferred catalysts are those which can form complexes of the "Lewis acid-base" type with the carbonyl compound to be oxidised, and which are not hydrolysed too rapidly under the reaction conditions, so as to have a life markedly greater than the average residence time of the reactants in the reactor.

The best results have been obtained with the fluorides of titanium, tantalum, tungsten, tin, antimony and zinc, the chlorides of tin, zinc perchlorate and boron fluoride complexed with an ether, such as $BF_3.O(C_2H_5)_2$, and hence the use of these compounds is preferred.

The catalysts employed can optionally be prepared in situ by reaction of the corresponding metal oxide, metal, metal-alkyls, metal alkoxides or, in general, metal salts. Thus, if metal fluorides are employed, hydrogen fluoride and an oxide of the selected metal can be introduced simultaneously into the reaction mixture. This technique has proved advantageous when the metal fluoride selected as the catalyst is difficult to dissolve in the reaction mixture. Such is the case, for example, for beryllium fluoride and zinc fluoride.

The catalysts employed can optionally be fixed to an organic or inorganic carrier.

The amount of catalyst employed is selected so as to ensure a stationary concentration which is sufficient to catalyse the reaction. In general, at least 0.001 g of catalyst is employed per kg of reaction mixture. Most commonly, the amounts of catalyst do not exceed 50 g per kg of reaction mixture, for economic reasons. Good results are obtained if the catalyst is employed at the rate of 0.01 to 20 g per kg of reaction mixture.

If the catalyst consists of hydrogen fluoride the amounts of catalyst required are in general greater and are between 0.01 and 100 g per kg of reaction mixture.

The catalysts can be introduced in various ways which are in themselves known. Thus, the catalysts can be introduced as a single shot, or continuously, or in stages. The catalyst can be employed in the pure state. However, it is advantageous to employ it in the form of a solution in one of the constituents of the reaction mixture.

In addition to the reactants and the catalysts, the reaction mixture can also contain—without this being essential—one or more solvents which are inert under the reaction conditions. Various types of inert solvents can be used. They can be selected from among the ethers, alcohols, halogenated hydrocarbons, unsubstituted hydrocarbons, carboxylic acid esters, non-acidic esters of phosphoric acid, hydrocarbons substituted by nitro groups, as well as certain ketones which are less reactive towards hydrogen peroxide under the reaction conditions, such as acetone.

As halogenated hydrocarbons which in general are very suitable there may be mentioned aromatic, aliphatic and alicyclic halogenated hydrocarbons which contain from 1 to 10 carbon atoms in their molecule, are substituted by at least one halogen preferably selected from among chlorine and fluorine, and can furthermore be substituted by a hydroxyl group.

As unsubstituted hydrocarbons which in general are very suitable there may be mentioned aliphatic, aromatic or alicyclic hydrocarbons containing from 5 to 14 carbon atoms.

As ethers which in general are very suitable there may be mentioned aliphatic or alicyclic, symmetrical or asymmetrical, ethers containing from 3 to 20 and preferably from 4 to 12 carbon atoms, such as diethyl ether, diphenyl ether, dimethoxy-monoethylene glycol or dimethoxy-diethylene glycol, tetrahydrofurane and diisopropyl ether.

As alcohols which in general are very suitable there may be mentioned monohydric or polyhydric primary, secondary or tertiary alcohols containing from 1 to 10 carbon atoms, such as ethanol and cyclohexanol.

As carboxylic acid esters which in general are very suitable there may be mentioned aliphatic esters containing from 3 to 9 carbon atoms in the molecule.

As hydrocarbons, substituted by nitro groups, which in general are very suitable there may be mentioned hydrocarbons containing from 1 to 10 carbon atoms such as nitromethane and nitrobenzene.

The phosphoric acid esters which can be used in general correspond to the formula

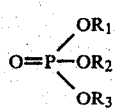

where $R_1$, $R_2$ and $R_3$ are identical or different and represent substituted or unsubstituted alkyl or aryl groups, such that the molecule contains from 3 to 30 carbon atoms. By way of specific examples of phosphates there may be mentioned triethyl phosphate and trioctyl phosphate.

If the water is difficult to remove from the reaction mixture, a solvent capable of forming a minimum boiling point azeotrope with the water can be incorporated into the mixture. In that case, a solvent capable of forming a heterogeneous azeotrope with water is generally used, so that the organic phase can be separated from the distillate of the azeotropic distillation, and can be recycled to the reactor.

The solvents, if any, are present in varying amounts which can range from 0 to 95% by weight of the reaction mixture. Where solvents are employed, they are in general present in amounts of from 30 to 95% by weight of the reaction mixture. For the oxidation of cyclohexanone, inert solvents are generally not used.

It is also possible to introduce other additives into the reaction mixture, such as hydrogen peroxide stabilisers, polymerisation inhibitors or inorganic or organic derivatives which can fix the water present in the reaction mixture. These optional additives are in general present in amounts of less than 10% by weight of the reaction mixture.

The reaction temperature and the reaction pressure can vary within very wide limits. They are chosen in accordance with the nature of the carbonyl compound to be oxidised. In general, they are regulated so as to ensure that the reaction mixture boils but that it does not rise above its decomposition temperature. The temperature is usually below 423° K. and most commonly between 293° and 393° K. Good results have been obtained at temperatures of between 313° and 373° K. The pressure is in general below $5.10^5$ Pa. Good results have been obtained by using pressures of between $1.10^3$ Pa and $3.10^5$ Pa.

The process according to the invention can be operated continuously or discontinuously in a single reactor or in a number of parallel or consecutive reactors. Any apparatus suitable for liquid reaction mixtures can be used for carrying out the process according to the invention. More particularly, it is advantageous to use reactors which are in themselves known and permit the distillation of constituents of a liquid reaction mixture during the reaction. These reactors are advantageously coupled to distillation columns which are in themselves known.

The process according to the invention can be carried out continuously in an apparatus such as that shown schematically in the single FIGURE of the attached drawing, which relates to a particular practical embodiment.

This apparatus is very particularly suitable for the oxidation of a carbonyl compound which is capable of forming a heterogeneous azeotrope with water, such as is the case for cyclohexanone.

A concentrated solution of hydrogen peroxide is introduced through line 3, and the carbonyl compound containing the catalyst is introduced through line 4, into a reactor 1 surmounted by a distillation column 2. The fresh carbonyl compound is introduced through line 5.

During the reaction, the water/carbonyl compound azeotrope leaves the distillation column 2 through line 9, is condensed in the condenser 10 and is fed through line 11 to the separating vessel 12. If the carbonyl compound has a lower density than that of water, the compound is collected at the top of the separating vessel through line 13, while the water is collected at the bottom of the separating vessel through line 14; in the converse case, the take-offs are reversed. The carbonyl compound is recycled to the distillation column through line 15, and constitutes the reflux in the column. In certain cases, a part of the carbonyl compound can be fed through line 16 into the mixer 6, which is fed with fresh carbonyl compound, and with catalyst, through line 5.

A part of the reaction mixture is withdrawn continuously through line 7 and is subjected to successive separations to obtain, on the one hand, the unconverted carbonyl compound, which is recycled to 6, and on the other hand, the carboxyl compound which constitutes the desired product.

The mixture withdrawn through line 7 can optionally be subjected to a preliminary treatment so as to make it possible to separate off the catalyst which may be contained therein. Thus, a strong Lewis base can be added to the mixture so as to complex the catalyst. Examples of Lewis bases which are suitable for this purpose are pyridine and 8-hydroxyquinoline. The complex thus formed is separated from the mixture and can subsequently be subjected to various catalyst regeneration steps which are in themselves known, such as a thermal decomposition. The regenerated catalyst can be recycled to the reactor for the preparation of the carboxyl compound.

The apparatus shown in the FIGURE can also be used to carry out the process of the invention in the presence of a solvent capable of forming, with water, a heterogeneous azeotrope having a boiling point lower than that of all the constituents and possible azeotropes of the reaction mixture. In this case, the organic phase collected in the separating vessel 12 consists of the reaction solvent.

The carboxyl compounds obtained in accordance with the process of the invention can be used for the preparation of polymers such as polyesters, polyols or polyurethanes.

Examples of the preparation of carboxyl compounds (Examples 1 to 33, 35 and 37 to 49) are given below in order to illustrate the invention without however limiting its scope. Examples 34 and 36 are given by way of comparison.

EXAMPLE 1

The cyclohexanone is introduced into a double-jacket glass reactor heated by an oil circulation system and surmounted by a condenser kept at 263° K. $SbF_5$ is added at the rate of 0.2 g/kg of cyclohexanone (CHO), and the temperature is then raised to 363° K., and maintained at this value, under a pressure of $2.10^4$ Pa in order to distil the aqueous azeotrope. 95% strength $H_2O_2$ is then admitted, at a rate of 130 ml/hr.l, through a capillary tube. The distillation products are collected and determined by chromatography, as are the reaction products. The productivity in respect of ε-caprolactone (ε-CL) is 221 g/hr.l, with a selectivity, relative to $H_2O_2$, of 73%.

EXAMPLES 2 to 16

These experiments are carried out in a similar manner to Example 1.

The temperature and pressure are respectively 353° K. and $1.33 \times 10^4$ Pa, and the 95% strength $H_2O_2$ is diluted with a mixture of acetone and cyclohexanone in the ratio of 5/50/30 by volume. The feed rate of 95% strength $H_2O_2$ is 67 ml/hr.l. The duration of the experiment is about 30 minutes. The other working conditions, and the results obtained, are recorded in Table I.

TABLE I

| Experiment No. | Catalyst Nature | Concentration, g/kg of CHO | Productivity, g ε-CL/hr.l | Selectivity relative to $H_2O_2$, % |
|---|---|---|---|---|
| 2 | $SbF_5$ | 0.04 | 242 | 80 |
| 3 | $SbF_5$* | 0.4 | 208 | 69 |
| 4 | $SbCl_5$ | 0.5 | 81 | 41 |
| 5 | $SnCl_4$ | 0.2 | 190 | 63 |
| 6 | $BF_3.O(C_2H_5)_2$ | 1.2 | 242 | 80 |
| 7 | $SnF_4$ | 1.4 | 133 | 45 |
| 8 | $MoOCl_3.9,10$-P.Q.** | 0.4 | 189 | 62 |
| 9 | $SbF_3$ | 1.4 | 231 | 76 |
| 10 | $BF_3$ | 1.1 | 222 | 73 |
| 11 | $TiF_4$ | 0.7 | 169 | 56 |
| 12 | $MoO_2Cl_2$ | 0.4 | 187 | 62 |
| 13 | $MoCl_5$ | 0.2 | 185 | 61 |
| 14 | $BF_3.CH_3OH$ | 0.4 | 149 | 49 |
| 15 | $TaF_5$ | 0.4 | 164 | 54 |
| 16 | HF | 2.7 | 211 | 70 |

*The antimony pentafluoride is deposited on graphite (sold by Messrs. ALDRICH under the trademark GRAPHIMET) in an amount of 47% of the total weight of the catalyst.
**P.Q. = phenanthrenequinone With $SbF_5$, the average selectivity relative to cyclohexanone is 82%.

EXAMPLES 17 to 28

These experiments are carried out in a similar manner to Example 1.

The temperature and pressure are respectively 353° K. and $1.6 \times 10^4$ Pa, and the 84% strength $H_2O_2$ is diluted with a mixture of tetrahydrofurane and cyclohexanone in the ratio of 6/50/30 by volume. The feed rate of 84% strength $H_2O_2$ is 80 ml/hr.l. The other working conditions, and the results obtained, are recorded in Table II.

TABLE II

| Experiment No. | Catalyst Nature | Concentration g/kg of CHO | Productivity g ε-CL/hr.l | Selectivity relative to $H_2O_2$, % | Selectivity relative to CHO, % |
|---|---|---|---|---|---|
| 17 | $SbF_5$ | 0.079 | 231 | 75.9 | 84.7 |
| 18 | $SnCl_4$ | 0.3 | 209 | 68.8 | 91.7 |
| 19 | $BF_3.O(C_2H_5)_2$ | 1.2 | 242 | 79.5 | 78.3 |
| 20 | $SnF_4$ | 1.4 | 132 | 43.4 | 69.9 |
| 21 | $SbF_3$ | 1.4 | 234 | 76.9 | 92.1 |
| 22 | $BF_3$ | 0.7 | 233 | 76.7 | 90.8 |
| 23 | $TiF_4$ | 0.7 | 163 | 53.5 | 96.4 |
| 24 | $MoO_2Cl_2$ | 0.2 | 168 | 55.2 | 87.5 |
| 25 | $MoCl_5$ | 0.2 | 174 | 57.3 | 91.6 |
| 26 | $TaF_5$ | 0.4 | 222 | 73 | 91.3 |
| 27 | $WF_6$ | 0.035ml* | 236 | 77.5 | 84.7 |
| 28 | HF | 2.7 | 231 | 75.9 | 89.8 |

*The concentration is given in ml/kg of CHO.

EXAMPLES 29 to 32

These experiments are carried out in a similar manner to Example 1.

The catalysts are formed in situ by mixing the metal oxide with HF in the cyclohexanone.

The temperature and pressures are respectively 353° K. and $1.5 \times 10^4$ Pa, and the 95% strength $H_2O_2$ is diluted with a mixture of acetone and cyclohexanone in the ratio of 5/50/30 by volume. The feed rate of 95% strength $H_2O_2$ is 67 ml/hr.l. The other working conditions, and the results obtained, are recorded in Table III.

TABLE III

| Experiment No. | Catalyst Nature | Weight, g/kg of CHO | Productivity, g εCL/hr.l | Selectivity relative to H$_2$O$_2$, % |
|---|---|---|---|---|
| 29 | HF/ZnO | 0.3/0.3 | 189 | 62 |
| 30 | HF/Sb$_2$O$_3$ | 0.3/0.7 | 224 | 74 |
| 31 | HF/Sb$_2$O$_5$ | 0.3/0.5 | 222 | 73 |
| 32 | HF/ZnO | 2.7/3.4 | 235 | 77 |

EXAMPLES 33, 34, 35 and 36

The influence of the azeotropic removal of water on the performance of the catalysts is illustrated below.

Experiments 34 and 36, without removal of water, are carried out in accordance with Example 1, but under total reflux. The temperature and pressure are respectively 353° K. and $1.10^5$ Pa.

Experiments 33 and 35, with distillation of the azeotrope, are carried out in accordance with the procedure of Examples 2 to 16.

In all cases, the feed rate of 95% strength H$_2$O$_2$ is 67 ml/hr.l. The other working conditions and the results obtained are recorded in Table IV.

TABLE IV

| Experiment No. | Catalyst Nature | Concentration, g/kg of CHO | Removal of H$_2$O | Productivity, g ε-CL/hr.l | Selectivity relative to H$_2$O$_2$, % |
|---|---|---|---|---|---|
| 33 | HF | 2.7 | yes | 211 | 70 |
| 34 | HF | 2.7 | no | 65* | 28* |
| 35 | SbF$_5$ | 0.04 | yes | 242 | 80 |
| 36 | SbF$_5$ | 0.04 | no | 78* | 33* |

*For these two experiments, the degree of decomposition of H$_2$O$_2$ is less than 100%. These values are thus subject to error (in the sense of being too high).

EXAMPLE 37

This experiment is carried out under the conditions of Examples 17 to 28, using SbF$_5$ as the catalyst, 0.2 g/kg of cyclohexanone and 70% strength H$_2$O$_2$. The temperature and pressure are respectively 355° K. and $1.6 \times 10^4$ Pa and the 70% strength H$_2$O$_2$ is diluted with a mixture of tetrahydrofuran and cyclohexanone in the ratio of 7.5/50/30 by volume.

The feed rate of 70% strength H$_2$O$_2$ is 100 ml/hr.l.

The productivity in respect of ε-caprolactone is 225 g/hr.l, with a selectivity of 74% relative to H$_2$O$_2$.

EXAMPLE 38

This experiment is carried out under conditions similar to those of Examples 17 to 28. The concentration of the catalyst SbF$_5$ is 0.3 g/kg of cyclohexanone. The temperature and pressure are respectively 331° K. and $5.3 \times 10^3$ Pa and the 87% strength H$_2$O$_2$ is diluted with a mixture of tetrahydrofuran and cyclohexanone in the ratio of 6/50/30 by volume.

The feed rate of 87% strength H$_2$O$_2$ is 80 ml/hr.l.

The productivity in respect of ε-caprolactone is 214 g/hr.l, with a selectivity of 67% relative to H$_2$O$_2$.

EXAMPLE 39

This experiment is carried out under conditions similar to those of Examples 17 to 28. The ketone used is 2-methylcyclohexanone, and the catalyst, BF$_3$.O(C$_2$H$_5$)$_2$, is employed in an amount of 3.3 g/kg of ketone. The temperature and pressure are respectively 353° K. and $1.5 \times 10^4$ Pa and the 84% strength H$_2$O$_2$ is diluted with a mixture of tetrahydrofuran and 2-methylcyclohexanone in the ratio of 6/50/30 by volume.

The feed rate of 84% strength H$_2$O$_2$ is 60 ml/hr.l.

The productivity in respect of lactones is 180 g/hr.l, with a selectivity of 71% relative to H$_2$O$_2$.

EXAMPLE 40

This experiment is carried out under conditions similar to those of Examples 17 to 28. The ketone used is cyclopentanone, and the catalyst, BF$_3$.O(C$_2$H$_5$)$_2$, is employed in an amount of 4.0 g/kg of ketone. The temperature and pressure are respectively 346° K. and $2.9 \times 10^4$ Pa and the 87% strength H$_2$O$_2$ is diluted with a mixture of tetrahydrofuran and cyclopentanone in the ratio of 6/50/30 by volume.

The feed rate of 87% strength H$_2$O$_2$ is 60 ml/hr.l.

The productivity in respect of δ-valerolactone is 103 g/hr.l, with a selectivity of 49% relative to H$_2$O$_2$.

EXAMPLE 41

This experiment is carried out under conditions similar to those of Examples 17 to 28, using a solution of cyclohexanone in diphenyl ether, of concentration 469 g/kg. BF$_3$.O(C$_2$H$_5$)$_2$ is used as the catalyst (3.2 g/kg of cyclohexanone) and 87% H$_2$O$_2$ is employed. The temperature and pressure are respectively 383° K. and $9.3 \times 10^3$ Pa and the 87% strength H$_2$O$_2$ is diluted with a mixture of tetrahydrofuran and cyclohexanone in the ratio of 6/50/30 by volume.

The feed rate of 87% strength H$_2$O$_2$ is 80 ml/hr.l.

The productivity in respect of ε-caprolactone is 183 g/hr.l, with a selectivity of 58% relative to H$_2$O$_2$.

EXAMPLE 42

This experiment is carried out under the conditions of experiment 41, except that a solution of cyclohexanone in 1,1,2,2-tetrachloroethane, of concentration 374 g/kg, is employed. The temperature and pressure are respectively 385° K. and $1.3 \times 10^4$ Pa.

The productivity in respect of ε-caprolactone is 220 g/hr.l, with a selectivity of 69% relative to H$_2$O$_2$.

EXAMPLE 43

This experiment is carried out under similar conditions to those of Example 1 but the volume in the reactor is kept constant by continuous addition of cyclohexanone. SbF$_5$ is used as the catalyst (0.2 g/kg of cyclohexanone) and 41% strength H$_2$O$_2$ is employed. The temperature and pressure are respectively 357° K. and $1.4 \times 10^4$ Pa.

The feed rate of 41% strength H$_2$O$_2$ is 462 ml/hr.l.

The productivity in respect of ε-caprolactone is 489 g/hr.l, with a selectivity of 67% relative to H$_2$O$_2$.

EXAMPLE 44

This experiment is carried out under the working conditions of Example 43, but the cyclohexanone added contains 0.08 g of catalyst/kg of cyclohexanone and the H$_2$O$_2$ used is of 20% strength. The temperature and pressure are respectively 355° K. and $1.4 \times 10^4$ Pa.

The feed rate of 20% strength H$_2$O$_2$ is 244 ml/hr.l.

The productivity in respect of ε-caprolactone is 104 g/hr.l, with a selectivity of 57% relative to H$_2$O$_2$.

EXAMPLE 45

This experiment is carried out under similar conditions to Experiment 44, but with 69% strength $H_2O_2$. The temperature and pressure are respectively 363° K. and $1.4 \times 10^4$ Pa.

The feed rate of 69% strength $H_2O_2$ is 242 ml/hr.l.

The productivity in respect of ε-caprolactone is 534 g/hr.l, with a selectivity of 75% relative to $H_2O_2$.

EXAMPLE 46

This experiment is carried out under similar conditions to Experiment 44, but with 86% strength $H_2O_2$. The temperature and pressure are respectively 364° K. and $1.4 \times 10^4$ Pa.

The feed rate of 86% strength $H_2O_2$ is 171 ml/hr.l.

The productivity in respect of ε-caprolactone is 510 g/hr.l, with a selectivity of 76% relative to $H_2O_2$ and a selectivity of 85% relative to cyclohexanone.

EXAMPLE 47

This experiment is carried out under conditions similar to Experiment 43, but with 86% strength $H_2O_2$, and using $SbF_3$ as the catalyst (1.4 g/kg of cyclohexanone). The temperature and pressure are respectively 362° K. and $1.3 \times 10^4$ Pa.

The feed rate of 86% strength $H_2O_2$ is 141 ml/hr.l.

The productivity in respect of ε-caprolactone is 420 g/hr.l, with a selectivity of 76% relative to $H_2O_2$ and a selectivity of 88% relative to cyclohexanone.

EXAMPLE 48

The cyclohex-2-en-1-one is introduced into a reactor similar to that of Example 1. $SbF_5$ is added in an amount of 0.2 g/kg of ketone and the temperature is then raised to 369° K., and kept at this value, under a pressure of $8 \times 10^3$ Pa. 86% strength $H_2O_2$ is then introduced at a rate of 267 ml/hr.l.

The productivity in respect of lactones is 348 g/hr.l, with a selectivity of 34% relative to $H_2O_2$.

EXAMPLE 49

The heptanal is introduced into a reactor similar to that of Example 1. $BF_3.O(C_2H_5)_2$ is added in an amount of 2.7 g/kg of aldehyde, and the temperature is then raised to 351° K. and kept at this value, under a pressure of $1 \times 10^4$ Pa. 86% strength $H_2O_2$ is then introduced at a rate of 267 ml/hr.l.

The productivity in respect of heptanoic acid is 671 g/hr.l, with a selectivity of 58% relative to $H_2O_2$.

EXAMPLE 50

A 50% strength solution of cyclododecanone in 1,1,1,2-tetrachloroethane is introduced into a reactor similar to that of Example 1. $BF_3.O(C_2H_5)_2$ is added in an amount of 4.6 g/kg of ketone, and the temperature is then raised to 347° K. and kept at this value, under a pressure of $1.0 \times 10^4$ Pa. 86% strength $H_2O_2$ is then introduced at a rate of 185 ml/hr.l.

Examination by nuclear magnetic resonance shows a lactone content of 7% relative to cyclododecanone.

EXAMPLE 51

The cyclohexanone is introduced into a reactor similar to that of Example 1. $Zn(ClO_4)_2.6H_2O$ is added in an amount of 7.0 g/kg of ketone and the temperature is then raised to 353° K. and kept at this value, under a pressure of $1.1 \times 10^4$ Pa. 86% strength $H_2O_2$ is then introduced at a rate of 218 ml/hr.l.

The productivity in respect of ε-caprolactone is 472 g/hr.l, with a selectivity of 55% relative to $H_2O_2$.

What is claimed is:

1. In a process for the oxidation of a carbonyl compound in a liquid reaction mixture to form the corresponding carboxyl compound, wherein the carbonyl compound is selected from the group consisting of substituted or unsubstituted, saturated or unsaturated, aliphatic or alicyclic ketones and aldehydes, and wherein the corresponding carboxyl compound is a carboxylic acid when the carbonyl compound is an aldehyde, an ester when the carbonyl compound is a ketone, and a lactone when the carbonyl compound is a cyclic ketone, by reacting the carbonyl compound with hydrogen peroxide in the liquid reaction mixture, and in the presence of a catalyst, the improvement comprising maintaining the liquid reaction mixture in a substantially anhydrous state.

2. Process according to claim 1, wherein the carbonyl compound is an aldehyde and the carboxyl compound is a carboxylic acid.

3. In a process for the oxidation of a cyclic ketone in a liquid reaction mixture to form the corresponding lactone, by reacting the cyclic ketone with hydrogen peroxide in the liquid reaction mixture, and in the presence of a catalyst, the improvement comprising maintaining the liquid reaction mixture in a substantially anhydrous state.

4. Process according to claim 1 or 3 a water concentration of less than 2% by weight is maintained in the reaction mixture.

5. Process according to claim 1 or 3, wherein the reaction mixture is maintained in a substantially anhydrous state by continuously removing water therefrom by vaporisation.

6. Process according to claim 1 or 3, wherein at least one Friedel-Crafts catalyst is employed as the catalyst.

7. Process according to claim 6, wherein the catalyst is selected from the group consisting of hydrogen fluoride and the compounds of the metals beryllium, zinc, cadmium, boron, aluminum, gallium, indium, scandium, yttrium, lanthanum, silicon, germanium, tin, titanium, zirconium, hafnium, thorium, antimony, bismuth, vanadium, niobium, tantalum, tellurium, chromium, molybdenum, tungsten, iron, ruthenium, and mixtures thereof.

8. Process according to claim 7, wherein the catalyst is selected from the group consisting of the fluorides of antimony, titanium, tantalum, tungsten, tin and zinc, zinc perchlorate, tin chloride and complexes of boron fluoride with an ether.

9. Process according to claim 1 or 3 wherein the catalyst is employed in amounts of between 0.001 and 50 g per kg of reaction mixture.

10. Process according to claim 1 or 3, wherein said reaction mixture contains from 0.001 to 10% by weight of hydrogen peroxide and from 5 to 99.9% by weight of the carbonyl compound.

11. Process according to claim 1 or 3, wherein the reaction mixture additionally contains a solvent.

12. Process according to claim 1 or 3 applied to the preparation of ε-caprolactone by reaction of cyclohexanone.

13. Process according to claim 12, wherein the reaction mixture is maintained in a substantially anhydrous state by removing water therefrom by distillation of a water-cyclohexanone azeotrope, the distillate is condensed and allowed to settle out so that an aqueous phase can be separated from an organic phase, and the organic phase is recycled to the reaction mixture.

* * * * *